United States Patent
Dalvit (10) Patent No.: US 12,216,084 B2
(45) Date of Patent: Feb. 4, 2025

(54) METAL DEBRIS SENSOR FOR OIL WITH TEMPERATURE COMPENSATION

(71) Applicant: DANA ITALIA S.R.L., Trentino (IT)

(72) Inventor: Bruno Dalvit, Arco (IT)

(73) Assignee: DANA ITALIA S.R.L., Arco (IT)

( * ) Notice: Subject to any disclaimer, the term of this patent is extended or adjusted under 35 U.S.C. 154(b) by 321 days.

(21) Appl. No.: 17/655,457

(22) Filed: Mar. 18, 2022

(65) Prior Publication Data

US 2023/0296562 A1 Sep. 21, 2023

(51) Int. Cl.
*G01N 27/90* (2021.01)
*G01N 33/28* (2006.01)

(52) U.S. Cl.
CPC ..... *G01N 27/9006* (2013.01); *G01N 33/2858* (2013.01)

(58) Field of Classification Search
CPC .............. G01N 27/9006; G01N 33/2858
See application file for complete search history.

(56) References Cited

U.S. PATENT DOCUMENTS

| | | | | |
|---|---|---|---|---|
| 4,627,272 A | * | 12/1986 | Wright ................. | G01N 11/10 73/54.23 |
| 4,837,511 A | * | 6/1989 | Whittington ........... | G01V 3/102 324/327 |
| 5,262,732 A | | 11/1993 | Dickert et al. | |
| 5,604,441 A | | 2/1997 | Freese, V et al. | |
| 5,674,401 A | * | 10/1997 | Dickert .............. | G01N 33/2888 210/695 |
| 5,811,664 A | * | 9/1998 | Whittington ....... | G01N 15/0656 73/53.07 |
| 6,459,995 B1 | | 10/2002 | Collister | |
| 8,522,604 B2 | | 9/2013 | Zhe et al. | |
| 2003/0221911 A1 | * | 12/2003 | Eriksen ................. | F16C 41/008 184/6.4 |
| 2017/0002921 A1 | * | 1/2017 | Ture .................... | F16H 57/0404 |
| 2018/0030850 A1 | * | 2/2018 | Hagen ..................... | F16N 29/04 |
| 2018/0223907 A1 | * | 8/2018 | Ito ......................... | F16C 33/667 |
| 2019/0187036 A1 | * | 6/2019 | Barraclough ...... | G01N 15/1031 |
| 2020/0264135 A1 | * | 8/2020 | Rocco ..................... | G01N 27/74 |
| 2020/0325806 A1 | | 10/2020 | Worthen | |
| 2021/0260585 A1 | * | 8/2021 | Alabi ................ | B01L 3/502776 |
| 2021/0277955 A1 | * | 9/2021 | Ito ........................... | F16C 41/00 |
| 2022/0308037 A1 | * | 9/2022 | Haye ...................... | F01D 25/20 |
| 2023/0228731 A1 | * | 7/2023 | Szczesnowicz ........ | G01N 27/08 324/71.1 |

* cited by examiner

*Primary Examiner* — Helen C Kwok
(74) *Attorney, Agent, or Firm* — McCoy Russell LLP (57) ABSTRACT

Methods and systems are provided for an oil sensor. In one example, the oil sensor is a system for metallic debris detection, comprising a detection circuit including a first inductor and a second inductor, the second inductor shielded from the external environment, wherein the detection circuit generates an output based on a difference between a first voltage of the first inductor and a second voltage of the second inductor, where the difference indicates a presence of metallic debris within oil.

20 Claims, 8 Drawing Sheets

METAL DEBRIS SENSOR FOR OIL WITH TEMPERATURE COMPENSATION

TECHNICAL FIELD

The present description relates generally to a metal debris sensor for oil, and in particular, to an inductive metal debris sensor including temperature compensation.

BACKGROUND AND SUMMARY

Mechanical systems may include moving components such as bearings, gears, and the like, which can generate friction and heat during operation. As a result, mechanical wear may occur, and excessive mechanical wear may result in abnormal system operation. In order to lubricate and cool these components, which may assist in reducing mechanical wear, cooling and lubrication assemblies have been integrated within mechanical systems to direct oil to the components. In electric drive systems, oil circuits have been employed for routing oil to gearbox components, and separate coolant circuits are used to remove heat from electric motor components. The presence of oil in systems where lubrication of parts is desired may lubricate surfaces which come in contact with the oil and further take away some heat produced by friction of moving parts. Mechanical wear may still partially occur and metal particles from mechanical wear may be produced in the oil and follow the flow of oil to spread around the oil circuits. Metal particles (e.g., metal debris) may cause further mechanical wear and degradation of moving components of the mechanical system, thus a method is desired for identifying a presence of metal particles in lubricating oil. A measurement of accumulated metal debris may provide information about a working condition of the system, system element status, and may alert users to degradation of the oil prior to extensive damage of the system. Continuous real-time oil monitoring thus may assist in development of a predictive maintenance strategy. When metal particles are detected, a user may be alerted to the presence of metal particles and/or the mechanical system may perform methods to remove metal particles from the lubricating oil.

U.S. Pat. No. 5,262,732 from Dickert et. al. teaches an apparatus for detecting the degree of deterioration in lubricating oil, including a grid-like capacitive sensor that uses the lubricating oil as a dielectric medium, and a magnetic field imposed upon the oil to attract ferromagnetic wear particles into the vicinity of the sensor. The apparatus preferably includes using a permanent magnet and an electromagnet aligned to produce the magnetic field where the magnetic field produced by each magnet acts upon the oil along the same axis.

The inventors have recognized challenges to the above described apparatus and other systems for detecting the degree of deterioration in lubricating oil. For instance, in such systems, sources of voltage variations other than from metal particles may be present as a result of parasitic phenomena due to electronic components of the sensor and/or temperature variation of the sensor and/or system. Further, as the metal debris is suspended in oil, the metal debris follows the flow of oil throughout the system, which may result in further mechanical wear. Therefore, a sensor may be desired which detects deterioration of oil (e.g., for lubricating and, in some instances, at least partially cooling mechanical parts) without inference due to parasitic phenomena and/or temperature variation, and which removes the metal debris from the oil flow path.

To resolve at least a portion of the aforementioned issues, the inventors have developed a compact metal debris sensor for oil. In one example, the oil sensor is a system for metallic debris detection, comprising a detection circuit including a first inductor and a second inductor, the second inductor shielded from the external environment, wherein the detection circuit generates an output based on a difference between a first voltage of the first inductor and a second voltage of the second inductor, where the difference indicates a presence of metallic debris within oil.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The following description relates to an oil sensor. In one example, the oil sensor is a system for metallic (ferromagnetic) debris detection. The system may include a detection circuit including a first inductor and a second inductor, the second inductor shielded by the first inductor and an external case of the oil sensor. The detection circuit generates an output based on a difference between a first voltage of the first inductor and a second voltage of the second inductor, where the difference indicates a presence of metallic (ferromagnetic) debris within oil. In this way, a presence and quantity of metal debris may be detected in oil without interference from temperature or other parasitic voltage affecting elements. Thus, a level of oil degradation may be determined. Further degradation of oil and/or mechanical elements may be reduced using methods (e.g., beyond the scope of the herein described embodiment) which may be implemented following indication of oil degradation by the oil sensor.

Figure 1:
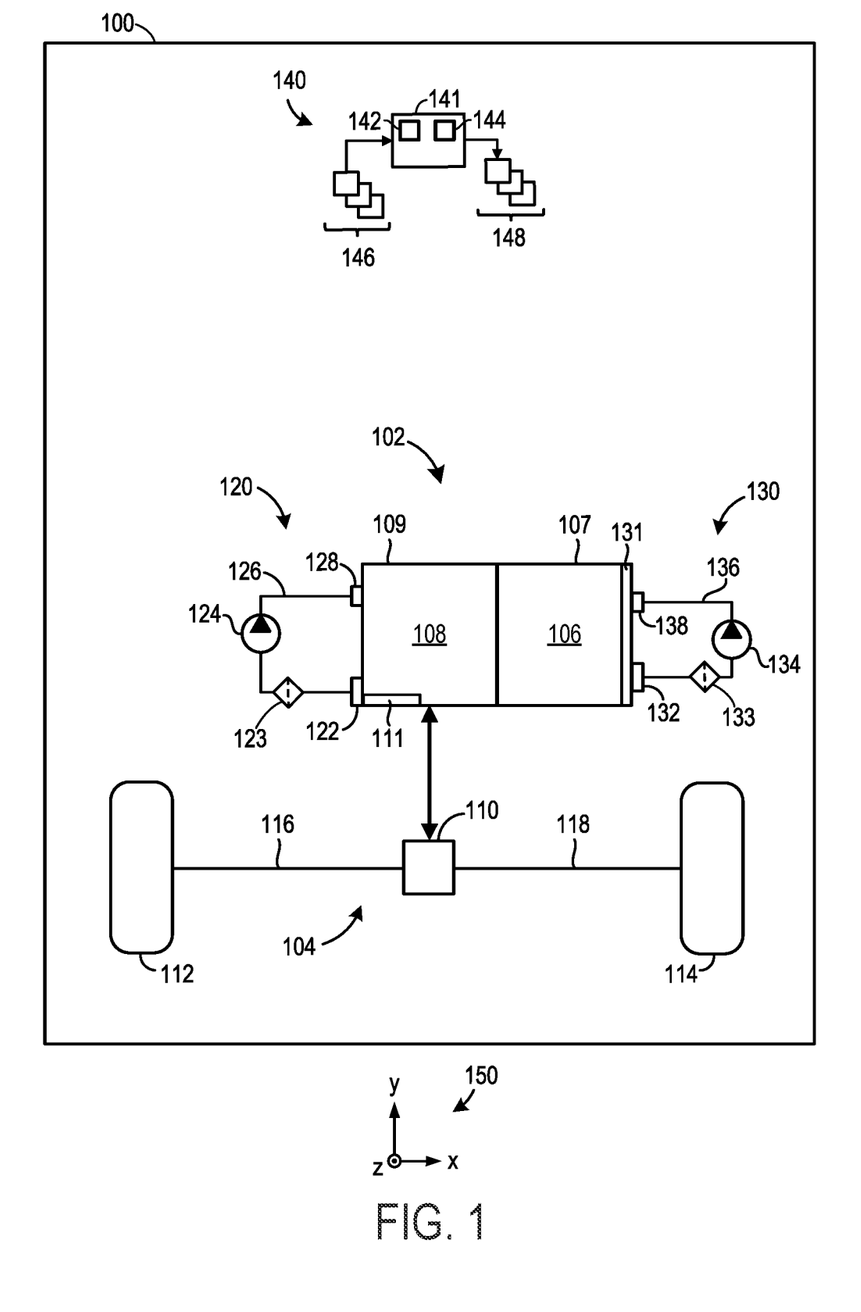
FIG. 1 shows a schematic representation of an electric drive system with lubrication and cooling assemblies.
Figure 2:
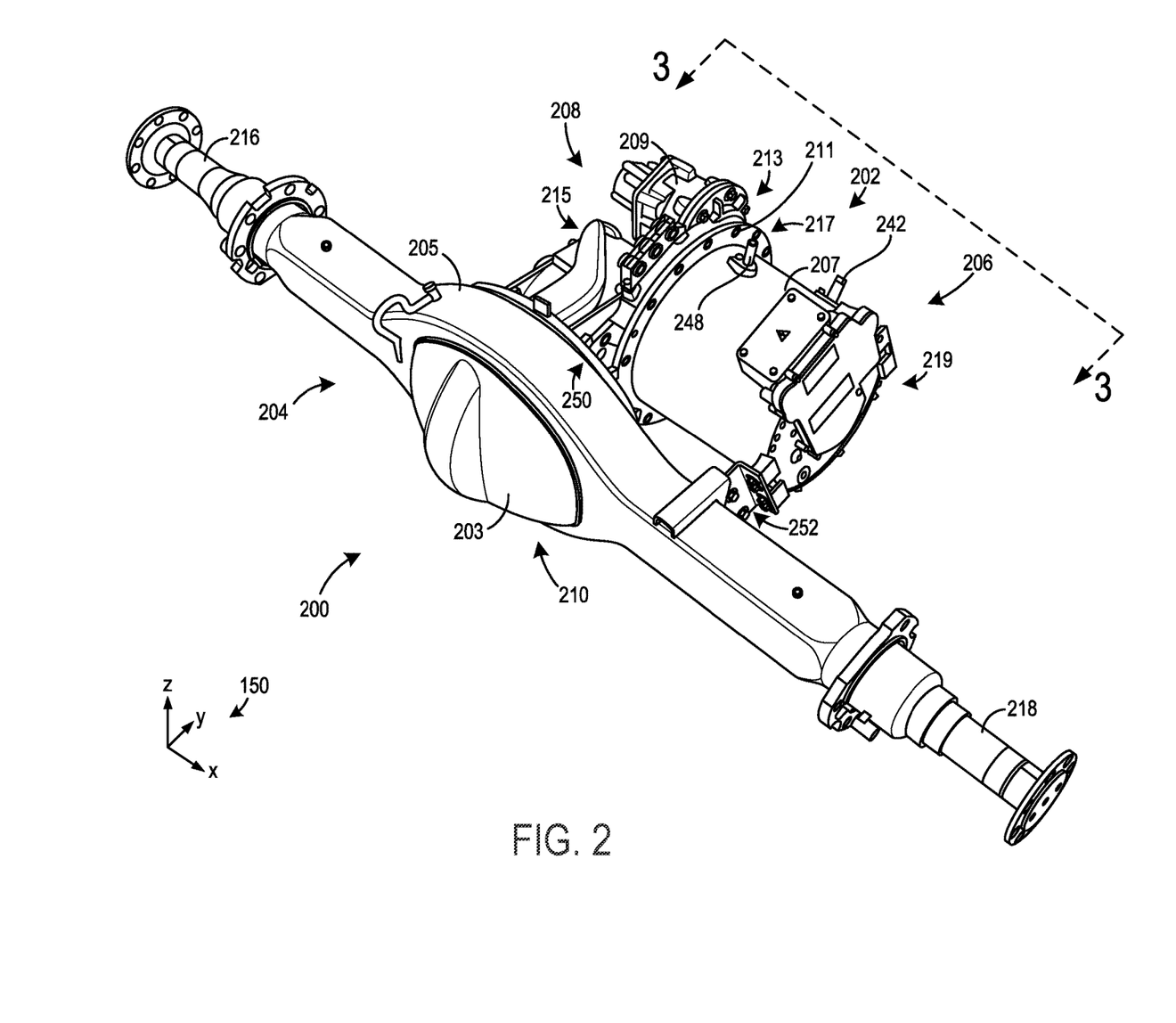
FIG. 2 shows a perspective view of an electric drive system, according to one example.
Figure 3:
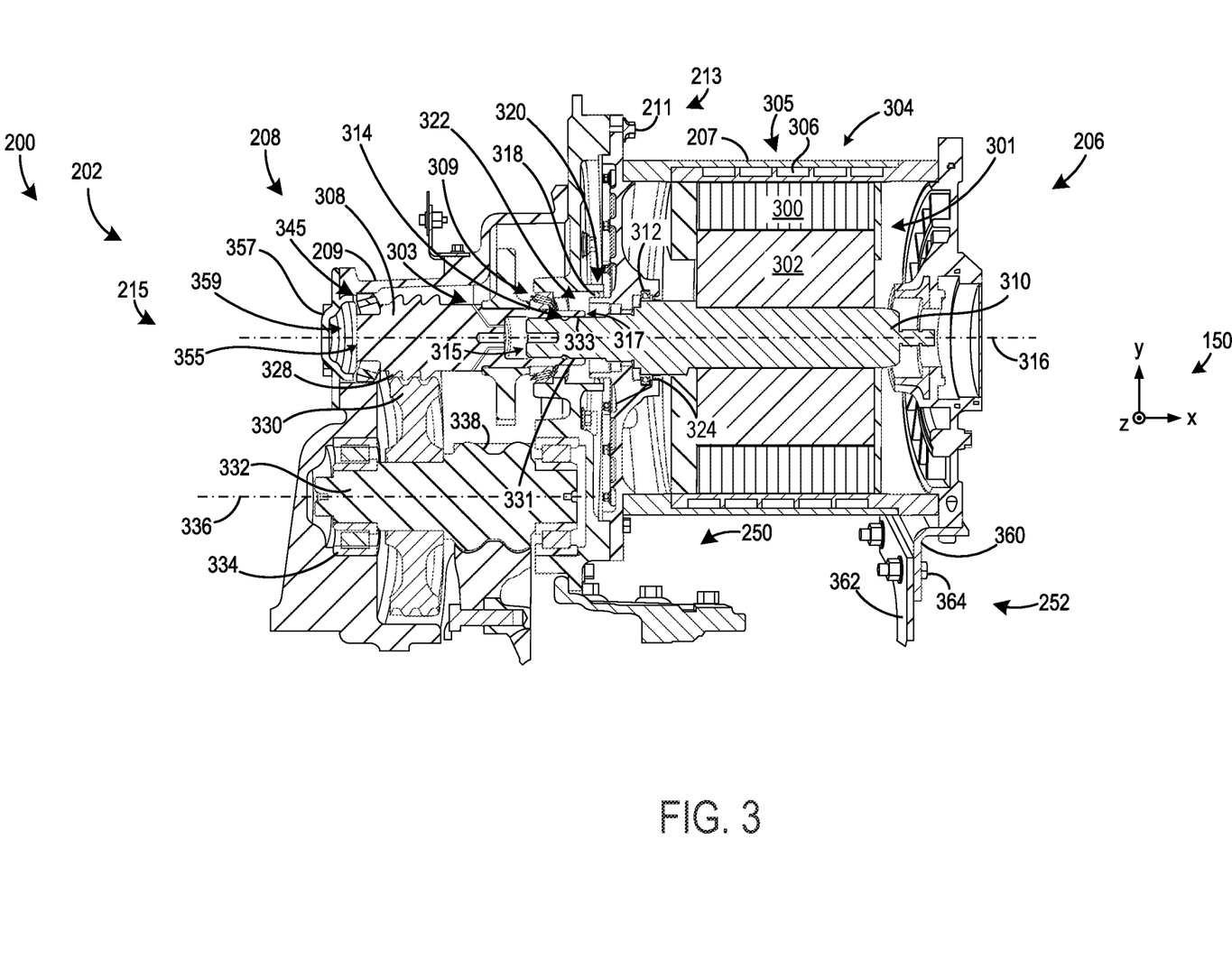
FIG. 3 shows a cross-sectional view of a portion of the electric drive system depicted in FIG. 2.
Figure 4:
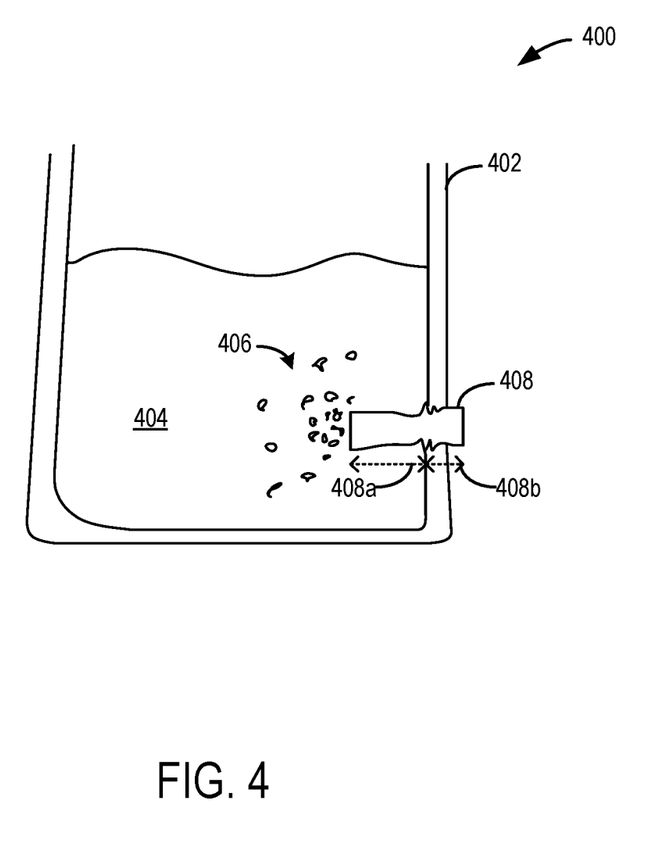
FIG. 4 shows an oil tank with an oil sensor, which may be implemented in the electric drive system depicted in FIGS. 2-3.

The oil sensor may be implemented in a system which includes an oil-lubricated part. For example, the oil sensor may be implemented in an electric drive system of a vehicle, as schematically depicted in FIG. 1. The electric drive system may include an oil circuit and a coolant circuit for cooling and lubrication of components in the system. FIG. 2 shows an electric drive system with an electric machine and a gearbox, which may be an example of the electric drive system of FIG. 1. FIG. 3 shows a cross-sectioned interior of the electric drive system of FIG. 2. The electric drive system includes an oil receptacle, such as an oil well or oil tank, which may have an oil sensor positioned at least partially therein, as shown in FIG. 4.

Figure 5:
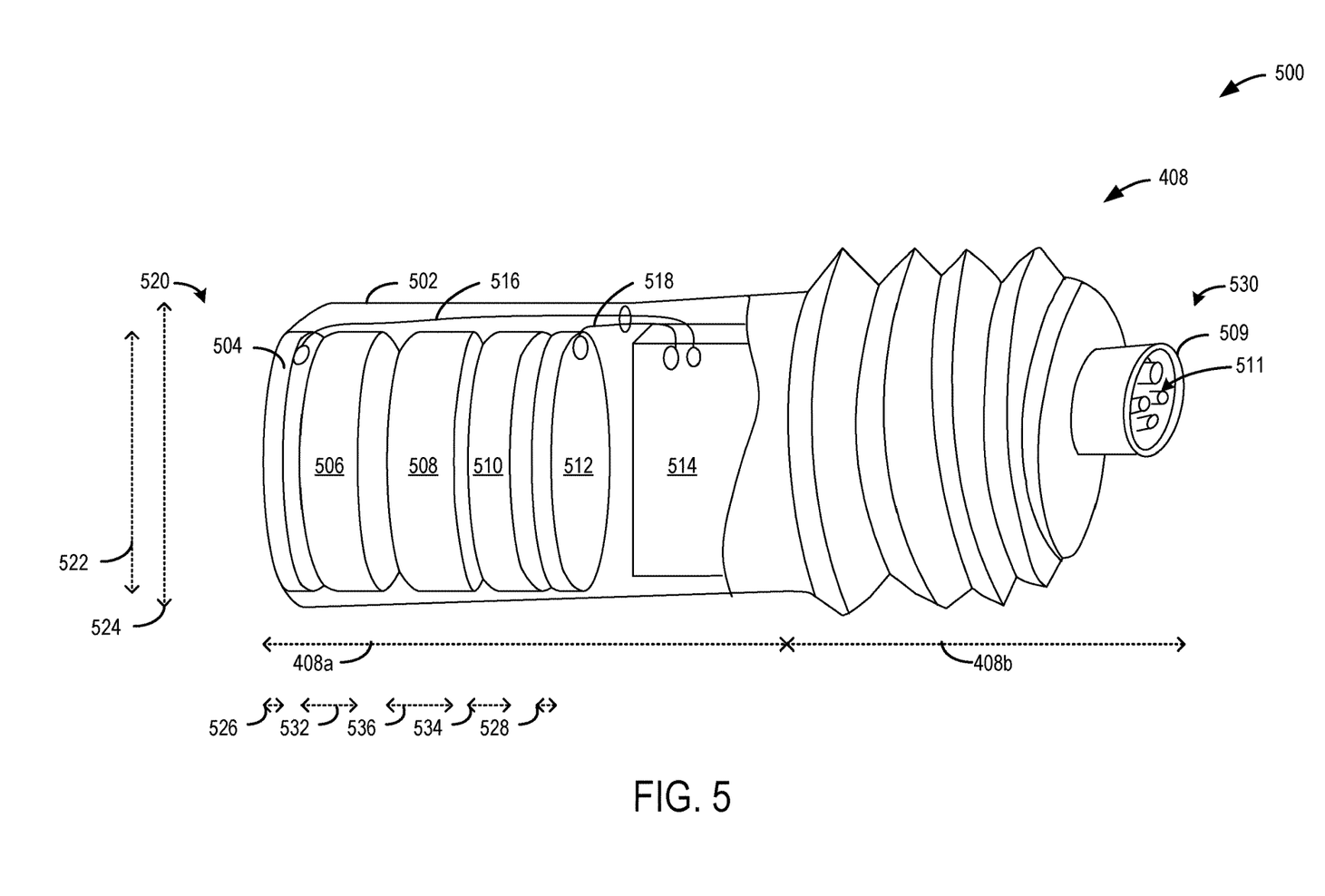
FIG. 5 shows a partial cross-sectional view of the oil sensor of FIG. 4.

The oil sensor may include components for detecting deterioration of oil due to metal debris in the oil, including a first inductor, a second inductor, a magnet, and a circuit board, as shown in FIG. 5. The circuit board may include circuitry, shown in FIG. 6, which allows for detection of metal debris in the oil based on a voltage difference of the first inductor and the second inductor. FIG. 7 details a method for detecting metal debris in the oil based on the voltage difference. The method of FIG. 7 may generate a voltage which may be used in a method of FIG. 8 to determine a quantity of metal debris in the oil and alert a user to a presence and quantity of metal debris in the oil. FIGS. 2-5 are drawn approximately to scale. However, other relative component dimensions may be used, in other embodiments.

As briefly described above, the oil sensor described herein may be used in systems having lubricated parts, such as mechanical drive systems, electric drive systems, and/or non-vehicle mechanical systems. Herein, the oil sensor is described as being implemented in an electric drive system, however the oil sensor may be implemented in other systems having lubricated parts. FIG. 1 schematically illustrates an electric vehicle 100 with an electric drive system 102 that provides power to and/or is incorporated into an axle assembly 104 vehicle 100. The vehicle 100 may take a variety of forms in different examples, such as a light, medium, or heavy duty vehicle. Additionally, the electric drive system 102 may be adapted for use in front and/or rear axles, as well as steerable and non-steerable axles. To generate power, the electric drive system 102 may include an electric machine 106. In some examples, the electric machine 106 may be an electric motor-generator and may thus include conventional components such as a rotor, a stator, and the like housed within an electric machine housing 107 for generating mechanical power as well as electric power during a regenerative mode, in some cases. Further, in other examples, the vehicle 100 may include an additional motive power source, such as an internal combustion engine (ICE) (e.g., a spark and/or compression ignition engine), for providing power to another axle. As such, the electric drive system 102 may be utilized in an electric vehicle (EV), such as a hybrid electric vehicle (HEV) or a battery electric vehicle (BEV).

In some examples, the electric machine housing 107 may be coupled (e.g., via bolts) to a housing 109 of a gearbox 108. Further, the electric machine 106 may provide mechanical power to a differential 110 via the gearbox 108. From the differential 110, mechanical power may be transferred to drive wheels 112, 114 by way of axle shafts 116, 118, respectively, of the axle assembly 104. As such, the differential 110 may distribute torque, received from the electric machine 106 via the gearbox 108, to the drive wheels 112, 114 of the axle shafts 116, 118, respectively, during certain operating conditions. In some examples, the differential 110 may be a locking differential, an electronically controlled limited slip differential, or a torque vectoring differential.

The gearbox 108 may be a single-speed gearbox, where the gearbox operates in one gear ratio. However, other gearbox arrangements have been envisioned such as a multi-speed gearbox that is designed to operate in multiple distinct gear ratios. Further, in one example, the electric machine 106, the gearbox 108, and the differential 110 may be incorporated into the axle assembly 104, forming an electric axle (e-axle) in the vehicle 100. The e-axle, among other functions, for provides motive power to the wheels 112, 114 during operation. Specifically, in the e-axle embodiment, the electric machine and gearbox assembly may be coupled to and/or otherwise supported by an axle housing. In one particular example, the e-axle may be an electric beam axle where a solid piece of material (e.g., a beam, a shaft, and/or a housing extend(s) between the drive wheels). The e-axle may provide a compact arrangement for delivering power directly to the axle. In other examples, however, the electric machine 106 and the gearbox 108 may be included in an electric transmission in which the gearbox and/or electric motor are spaced away from the axle. For instance, in the electric transmission example, mechanical components such as a driveshaft, joints (e.g., universal joints), and the like may provide a rotational connection between the electric transmission and the drive axle.

The electric drive system 102 may further include an oil circuit 120 for circulating oil (e.g., natural and/or synthetic oil) through the gearbox housing 109 to lubricate and/or cool various system components. The oil circuit 120 may include a filter 123 and an oil pump 124 that draws oil from an oil reservoir 111 (e.g., a sump) in the gearbox housing 109, via an outlet 122, and drives a pressurized oil flow through a delivery line 126 to an inlet 128 of the gearbox housing 109. As further described in FIGS. 2-6, the oil reservoir 111 may include an oil sensor for detecting deterioration of oil. In some examples, the oil pump 124 may be provided at an exterior portion of the gearbox housing 109. However, in other examples, the oil pump may be included within the housing 109. Various distribution components and arrangements (e.g., nozzles, valves, jets, oil passages, and the like) of the oil circuit 120 may be included within the electric drive system 102 in order to facilitate routing of the oil within the gearbox housing 109 and, in one particular example, to a portion of the electric machine housing 107. In some case, the oil circuit 120 may be used for routing oil to various gearbox shafts and gears as well as a rotor shaft bearing of the electric machine, thereby providing an efficient system for effectively using the gearbox oil to cool said bearing.

The electric drive system 102 may further include a coolant circuit 130 that circulates coolant (e.g., water and/or glycol) through a water jacket 131 formed in the electric machine housing 107. The coolant circuit 130 may include a coolant inlet 138 and a coolant outlet 132 positioned on (or in) the electric machine housing 107. The coolant circuit 130 may further include a filter 133 and a pump 134 that circulates coolant from the coolant outlet 132 to the coolant inlet 138 via a coolant delivery line 136. From the coolant inlet 138, the coolant travels into the water jacket 131 formed in the electric machine housing 107 which removes heat from components of the electric machine 106. In some examples, the coolant circuit 130 may further include a heat exchanger (e.g., radiator) which removes heat from the coolant that exits the electric machine housing 107 by way of the coolant outlet 132.

The vehicle 100 may also include a control system 140 with a controller 141. The controller 141 may include a processor 142 and a memory 144. The memory may be non-transitory memory and may hold instructions stored therein that when executed by the processor cause the controller 141 to perform various methods, control techniques, and the like described herein. The processor 142 may include a microprocessor unit and/or other types of circuits. The memory 144 may include known data storage mediums such as random access memory, read only memory, keep alive memory, combinations thereof, and the like. The controller 141 may receive various signals from sensors 146 positioned in different locations in the vehicle 100 and electric drive system 102. For example, sensors 146 may include the oil sensor described in FIGS. 4-6. The controller 141 may also send control signals to various actuators 148 coupled at different locations in the vehicle 100 and electric drive system 102. For instance, the controller 141 may send command signals to the oil pump 124 and/or the pump 134 and, in response, the actuator(s) in the pump(s) may be adjusted to alter the flowrate of the oil and/or coolant delivered therefrom. In other examples, the controller may send control signals to the electric machine 106 and, responsive to receiving the command signals, the electric machine may be adjusted to alter a rotor speed. The other controllable components in the system may be operated in a similar manner with regard to sensor signals and actuator adjustment.

An axis system 150 is provided in FIG. 1, as well as FIGS. 2-3, for reference. The z-axis may be a vertical axis (e.g., parallel to a gravitational axis), the x-axis may be a lateral axis (e.g., horizontal axis), and/or the y-axis may be a longitudinal axis, in one example. However, the axes may have other orientations, in other examples.

FIG. 2 depicts an example electric system 200 with an electric drive system 202 for providing power to an axle assembly 204. The electric drive system 202 may include an electric machine 206 operatively coupled to a gearbox 208 and may be included in a vehicle, such as the vehicle 100 depicted in FIG. 1, and may thus share similarities with the electric drive system 102. For instance, at least a portion of the components discussed with regard to the drive system 102, shown in FIG. 1, may be included in the electric drive system 202, shown in FIG. 2, or vice versa.

The electric machine 206 may include an electric machine housing 207 coupled to a gearbox housing 209 of the gearbox 208. In some cases, the electric machine housing 207 may be coupled to the gearbox housing 209 via fasteners, such as bolts 211, for instance. To elaborate, the gearbox housing 209 may have an inboard side 213, opposite an outboard side 215 thereof, coupled to an outboard side 217 of the electric machine housing 207, as illustrated in FIG. 2. Further, the electric machine housing 207 may include a coolant outlet 242 and a coolant inlet 248 of a coolant circuit (e.g., the coolant circuit 130 of FIG. 1) for moving coolant through a water jacket formed in the electric machine housing 207.

The electric machine 206 may provide power to a differential 210 via the gearbox 208 to provide rotational power to axle shafts 216, 218 (to which drive wheels may be coupled) of the axle assembly 204. In one example, the differential 210 and the axle shafts 216, 218 may be at least partially enclosed within an axle housing 205. In some examples, the axle housing 205 may include a differential cover 203 attachable thereto, near the differential, which may allow for access to the differential for maintenance, repair, etc. Further, the axle housing 205 and differential cover 203 may be designed so as to maintain a reservoir of oil in the vicinity of the differential 210, allowing for splash lubrication of components housed therein. The oil may be delivered to the axle housing 205 from the gearbox housing 209 (e.g., via an oil circuit similar to the oil circuit 120 of FIG. 1), which may also have a reservoir of oil collected in a bottom portion thereof. For example, the reservoir of oil in the gearbox housing 209 may be the oil reservoir 111 of FIG. 1, with the oil sensor positioned therein, as further described in FIG. 4.

The gearbox housing 209 may include a shaft and gearing arrangement housed therein for providing power to the differential 210 disposed within the axle housing 205. As such, the gearbox housing 209 may be fixedly mounted to the axle housing by any suitable attachment mechanism (e.g., bolts, brackets, welds, and/or combinations thereof) in a region adjacent to the differential 210, generally indicated as 250. Further, the electric machine housing 207 may be coupled to the axle housing 205, at a second location generally indicated as 252, by similar or other suitable mounting apparatuses. Other mounting arrangements have been envisioned, such as, for instance, where the electric machine housing 207 is not mounted to the axle housing 205 but rather suspended from the gearbox housing 209 in a cantilevered fashion. Such an arrangement, however, may provide less structural support to the electric machine.

The electric machine 206 and the gearbox 208 may thus be integrated with the axle assembly 204, in some examples, in an e-axle. Further, the axle housing 205, the electric machine housing 207, and the gearbox housing 209 may each be made of a metal (e.g., aluminum, steel, combinations thereof, and the like) which may be the same or a different metal for each housing.

FIG. 3 shows a partial cross-sectional view of the electric drive system 202 and axle assembly 204 shown in FIG. 2, as defined by a lateral cut taken along dashed line 3-3. FIG. 3 illustrates a portion of the electric drive system 202, including the electric machine 206 and gearbox 208. The electric machine 206 may include a stator 300 and a rotor 302 enclosed in a working chamber 301 of the electric machine housing 207.

The electric drive system 202 may further include an oil circuit 303 and a coolant circuit 305 that cool and/or lubricate electric machine and/or gearbox components, which may share similarities with the oil circuit 120 and the coolant circuit 130, respectively, depicted in FIG. 1. The electric machine housing 207 includes a water jacket 304 formed therein with coolant channels 306, which is included in the coolant circuit 305. The coolant channels 306 may receive coolant from upstream components in the coolant circuit 305, via an inlet formed in the electric machine housing 207, as previously discussed with regard to the coolant circuit 130 of FIG. 1. The coolant circulating through the water jacket 304 may function to remove heat from the stator, rotor, and bearings of the electric machine 206.

The rotor 302 is designed to electromagnetically interact with the stator 300 to provide torque to a gearbox shaft 308 (e.g., a gearbox input shaft) via a rotor shaft 310. The rotor shaft 310 may be supported for rotation in the electric machine housing 207 by bearings positioned at outboard and inboard ends thereof. In the frame of reference depicted in FIG. 3, the inboard and outboard ends of the rotor shaft are the right and left ends, respectively. In particular, a front rotor shaft bearing 312 is shown disposed on the rotor shaft 310 near the outboard end thereof proximal to the gearbox 208. In some examples, the rotor shaft bearing 312 may be a radial bearing, such as a spherical ball bearing. More generally, the rotor shaft bearing 312 may include an inner race, an outer race, and rolling elements (e.g., rollers or spherical balls). The inner race of the bearing 312 is in contact with the rotor shaft 310 and the outer race may be in contact with the electric machine housing 207.

The gearbox shaft 308 may be supported for rotation in the gearbox housing 209 by a gearbox shaft bearing 309. As such, the bearing 309 is positioned on the gearbox shaft 308. In some cases, the bearing 309 may have a different configuration than the rotor shaft bearing 312. For instance, the bearing 309 may be a thrust bearing, such as a tapered roller bearing. Thus, the design of the bearings 309 and 312 may be tailored to withstand the expected loading in the system, thereby increasing the system's longevity. The bearing 309 generally includes an inner race, an outer race, and rolling elements (e.g., tapered rollers). As such, the inner race is in contact with the gearbox shaft 308 and the outer race may be in contact with the gearbox housing 209.

In one example, as illustrated in FIG. 3, the electric machine housing 207 of the electric machine 206 may be coupled to the gearbox housing 209 of the gearbox 208 by way of bolts 211. For instance, an inboard side 213 of the gearbox may be coupled to the motor housing. Further, the gearbox shaft 308 may be coupled for rotation with the rotor shaft 310, such that a shaft interface 314 is formed therebetween within the gearbox housing 209. Specifically, the shaft interface 314 is formed between an outboard end 315 of the rotor shaft 310 and an inboard end 317 of the gearbox shaft 308. In the frame of reference illustrated in FIG. 3, the inboard end of the gearbox shaft is the right end of the shaft and the outboard end is the left end of the shaft.

In some examples, the shaft interface 314 may be a splined interface. In such an example, each of the rotor shaft 310 and the gearbox shaft 308 may have a plurality of splines that extend axially along a portion thereof, at the outboard end 315 and the inboard end 317, respectively. Specifically, in one example, the rotor shaft 310 may have splines disposed on an exterior surface 331 at a portion of the outboard end 315 thereof. The outboard end of the rotor shaft is the rotor shaft's left end in the frame of reference illustrated in FIG. 3. The gearbox shaft 308 may have splines on an interior surface 333 along a portion of the inboard end 317 thereof. The splines on the gearbox and rotor shafts axially extend along a length of the corresponding shaft. Additionally, the rotor shaft 310 and the gearbox shaft 308 are coaxially disposed and therefore have a common rotational axis 316.

In some examples, a housing seal 318 may be disposed between the electric machine housing 207 and the gearbox housing 209. More specifically, the housing seal 318 may be disposed at a housing interface 320 (between the electric machine housing 207 and the gearbox housing 209) in the vicinity of the splined shaft interface 314. Further, the housing seal 318 may form a portion of a boundary of a sealed cavity 322. Oil may be introduced into the sealed cavity 322 through oil passages in the shaft interface 314 and from the sealed cavity oil flows to the front rotor shaft bearing 312. Other boundaries of the sealed cavity 322 may include a portion of an interior surface of the gearbox housing 209 and a portion of an interior surface of the electric machine housing 207, a portion of an outer surface of the gearbox shaft 308, and/or a portion of an outer surface of the rotor shaft 310. In one example, the sealed cavity 322 may be bounded by a rotor shaft seal 324 positioned on an inboard side of the rotor shaft bearing 312. The sealed cavity 322 may be the oil reservoir 111 of FIG. 1 and have the oil sensor positioned at least partially therein. Details of the sealed cavity 322 and the oil sensor are expanded upon with reference to FIGS. 4-6.

Returning to FIG. 3, the gearbox shaft 308 may have a gear 328 formed thereon outboard of the bearing 309, proximate an outboard end 355 of the gearbox shaft. A bearing 345 may be coupled to the outboard end 355 of the gearbox shaft 308. To elaborate, the bearing 345 may include an outer race that contacts the gearbox housing 209 and an inner race that is disposed around the gearbox shaft 308. Further, in some examples, a cover 357 may be coupled to the side 215 of the gearbox housing 209 at a position corresponding to the outboard end 355 of the gearbox shaft 308, such that an oil chamber 359 is formed between the cover 357 and the outboard end of the gearbox shaft. In some cases, this oil chamber 359 may receive and at least partially retain oil for subsequent routing through the gearbox housing and components. The oil chamber 359 may be an additional or alternative example of the oil reservoir 111 of FIG. 1, and have the oil sensor positioned at least partially therein.

As depicted in FIG. 3, the gear 328 may be in meshing engagement with a first gear 330 which is disposed on a shaft 332 (e.g., a gearbox output shaft), so that rotational power from the rotor shaft 310 may be transferred to the gearbox shaft 308 and then to the shaft 332 by way of the meshing gears 328, 330. The shaft 332 may be supported within the gearbox housing 209 by a pair of bearings 334 (e.g., roller bearings, such as cylindrical or spherical roller bearings) positioned on opposing axial ends of the shaft. Further, the shaft 332 may have a rotational axis 336 which is parallel to, and offset from, the common rotational axis 316 of the rotor shaft and gearbox shaft. However, other gearbox configurations have been contemplated. For instance, the shaft 332 may be omitted from the gearbox and power may be transferred directly from the shaft 308 to the differential 210, shown in FIG. 2.

The shaft 332 may have a second gear 338 formed thereon and in meshing engagement with an input gear of the differential 210 of FIG. 2. Thus, rotational power received at the shaft 332 may be transferred to the input gear of the differential via the second gear 338, whereby rotational power may be distributed to the axle shafts 216, 218 of the axle assembly 204 and eventually to drive wheels (e.g., the wheels 112, 114 of FIG. 1), in some examples. The gearbox housing 209 may be attached to the axle housing as generally indicated at location 250. Further, the electric machine housing 207 may also be coupled to the axle housing 205 at a location 252, different from location 250. In one example, location 250 may be proximate an inboard side 219 of the electric machine housing 207, opposite the outboard side 217 of the electric machine housing. Further, a bracket 360 on the electric machine housing 207 may be joined to a bracket 362 on the axle housing 205 via bolts 364, though other suitable fastening arrangements have been contemplated.

The electric drive system described herein provides an efficient architecture for routing oil through a shaft interface between a rotor shaft and a gearbox shaft to cool and lubricate a front rotor shaft bearing disposed within an electric machine housing. When mechanical wear occurs to elements of the electric drive system, metal debris may become suspended in the oil and flow through the lubrication system, which may further degrade elements of the electric drive system. An oil sensor, further described in FIGS. 4-6, may be at least partially positioned in an oil reservoir, such as the oil reservoir 111 of FIG. 1, examples of which may be at least one of the sealed cavity 322 or the oil chamber 359 of FIG. 3. The oil sensor may infer a presence of metal debris in the oil and prevent metal debris from circulating with the flow of oil using two inductors with an associated detection circuit, further described in FIGS. 4-6.

As previously described, the oil sensor is at least partially positioned in an oil reservoir of a lubricating circuit, such as the oil reservoir 111 of FIG. 1, which may be at least one of the sealed cavity 322 or the oil chamber 359 of FIG. 3. FIG. 4 shows an embodiment 400 of an oil reservoir 402 with an oil sensor 408 positioned at least partially therein. In the example of FIG. 4, the oil sensor 408 is positioned in a vertical wall of the oil reservoir 402 such that a first region 408a of the oil sensor 408 is in an interior of the oil reservoir 402 and a second region 408b of the oil sensor 408 is in the vertical wall and extends to an exterior of the oil reservoir 402.

The oil reservoir 402 may contain a volume of oil 404 such that the first region 408a of the oil sensor 408 is submerged in the oil 404. The oil 404 may have metal debris 406 suspended therein. Metal debris 406 may be generated as a result of mechanical wear throughout the electric drive system shown in FIGS. 1-3. The metal debris 406 may be generated at a point of mechanical wear, e.g., at a physical interface between metal elements of the electric drive system. The metal debris 406 may then follow a flow of oil through the lubrication circuit (e.g., of FIG. 1) to the oil reservoir 402. As further described in FIG. 5, a magnet of the oil sensor 408 may attract the metal debris 406 such that it may be held at the oil sensor 408 and not circulate through the lubrication circuit with the oil 404. The oil 404 may circulate through the lubrication circuit as described in FIGS. 1-3.

FIG. 5 shows a partial cross-sectional view 500 of the oil sensor 408 of FIG. 4. The first region 408a is shown with an external case 502 partially cut away, however the external case 502 may completely surround the oil sensor 408, thus forming a barrier between internal elements of the oil sensor 408 and air and/or oil, and the partial cut is shown for illustration purposes. The external case 502 may be formed of a material which may shield a second inductor 512, herein also referred to as an internal sensing element, from metal debris influences. For example, the external case 502 may be formed of metal or other non-magnetically inert material. The material forming the external case 502 may prevent metal debris from accumulating on an external surface (e.g., a surface in contact with oil) of the external case 502. At least a portion of the external case 502 in proximity to the second inductor 512 may be formed of a material other than plastic, as plastic may not sufficiently shield the second inductor 512 from an influence of accumulated metal debris. Influence of accumulated metal debris is further described herein.

The second region 408b of the external case 502 may be formed as a screw, which may allow the oil sensor 408 to be positioned in the wall of the oil reservoir, as shown in FIG. 4. The external case 502 may further include a connector 509 having a plurality of connectors 511 therein. The plurality of connectors 511 may allow the oil sensor 408 to be in wired or wireless communication with a control system, such as the control system 140 of FIG. 1, as further described in FIGS. 6-7.

Within the external case 502, the oil sensor 408 includes a first inductor 504, a first spacer 506, a magnet 508, a second spacer 510, and the second inductor 512. The first spacer 506 and the second spacer 510 may be formed of plastic or another magnetically inert, nonconductive material. The first inductor 504 and the second inductor 512 may have the same structure. For example, the first inductor 504 and the second inductor 512 may each be a four-layer spiral. The four-layer spiral may be made of coiled wire, such as copper or other conductive metal wire. The magnet 508 may be formed by any magnetic material capable of attracting metal or other metallic (e.g., ferromagnetic) debris.

The first inductor 504 may be positioned at a first end 520 of the oil sensor 408, where the first end is in contact with oil (e.g., the oil 404 in the oil reservoir 402 of FIG. 4). In one example, the first inductor 504 is contained (e.g., separated from the oil) by the external case 502. In a second example, a surface of the first inductor 504 in alignment with the first end 520 of the external case 502 is exposed to, and therefore in contact with, the oil.

In a direction towards a second end 530 of the oil sensor 408 opposite the first end 520, the first spacer 506 is positioned next to the first inductor 504, followed by the magnet 508, the second spacer 510, and the second inductor 512. Each element may be positioned in face sharing contact with the element on either side (e.g., the first spacer 506 is in face sharing contact with the first inductor 504 and the magnet 508). In another example, there may be a space between each of the elements.

In one example, the first inductor 504, the first spacer 506, the magnet 508, the second spacer 510, and the second inductor 512 have approximately a height 522, which is less than a height 524 of the first region 408a of the oil sensor 408. Further, the first inductor 504, the first spacer 506, the magnet 508, the second spacer 510, and the second inductor 512 may be positioned with a center point of each element in an approximate middle of the height 524. In one example, a first width 526 of the first inductor 504 is approximately equal to a second width 528 of the second inductor 512. A third width 532 of the first spacer 506 may be greater than, less than, or equal to a fourth width 534 of the second spacer 510. The third width 532 and the fourth width 534 may both be greater than the first width 526 and the second width 528. The magnet 508 may have a fifth width 536, which may be greater than the first width 526 and the second width 528, and may be greater than, less than, or equal to the third width 532.

The oil sensor 408 further includes a circuit board 514, which may extend into the second region 408b. The first inductor 504 may be coupled to the circuit board 514 via a first cable 516 and the second inductor 512 may be coupled to the circuit board 514 via a second cable 518. For example, the first cable 516 and the second cable 518 may be electrical lead connections. The circuit board 514 may be used to help stimulate a first inductance and a second inductance (e.g., of the first inductor and the second inductor, respectively) and to condition an output signal, as further described in FIG. 6.

Briefly, the oil sensor 408 detects a presence of metal debris in oil (e.g., as shown in FIG. 4) by identifying a peak voltage using the first inductor 504 and the second inductor 512. For example, each of the first inductor 504 and the second inductor 512 may have an electrical current flowing therethrough. The first inductor 504 is in contact with the oil and the second inductor 512 is physically shielded from voltage influences of the oil by the first inductor 504 and the external case 502, and may thus be used as a reference. The current flowing through the first inductor 504 and the second inductor 512 generates a magnetic field around each of the first inductor 504 and the second inductor 512.

The magnet 508 may have a stronger magnetic force than the magnetic fields of the first inductor 504 and the second inductor 512, and may pull metal debris in the oil towards the oil sensor 408. This may result in metal debris being held in place proximate to the first inductor 504, which may result in more accurate detection of metal debris compared to metal debris suspended in oil throughout the oil reservoir 402 of FIG. 4.

The magnetic field of the first inductor 504 may act on the metal debris and result in eddy currents in the metal debris. The eddy currents may result in changes to the magnetic field of the first inductor 504. Because the second inductor 512 is encapsulated in the external case 502 and placed behind each of the first inductor 504, the first spacer 506, the magnet 508, and the second spacer 510 (e.g., a distance between the first inductor 504 and the second end 530 is larger than a distance between the second end 530 and any of the first spacer 506, the magnet 508, the second spacer 510, or the second inductor 512), the second inductor 512 may be shielded from the magnetic field resulting from the eddy currents of the metal debris. For example, as the second inductor 512 is masked by the first inductor 504, eddy currents generated by the metal debris may not interfere with the magnetic field of the second inductor 512. Further, as the first inductor 504 and the second inductor 512 are formed of the same materials, they are similarly influenced by temperature. Due to being in close proximity, the first inductor 504 and the second inductor 512 are further similarly influenced by other potential external sources of noise (e.g., vibration due to vehicle movement). As one example, during conditions in which the oil temperature is higher, the conductivity of electrical current through components of the oil sensor 408 may be decreased. As a result, a strength (e.g., magnitude) of the magnetic fields of the first inductor 504 and second inductor 512 may be decreased. During conditions in which the oil temperature is lower, the conductivity of the electrical current through components of the oil sensor 408 may be increased. As a result, the strength of the magnetic fields of the first inductor 504 and second inductor 512 may be increased. In each of the conditions described above, however, because changes to the oil temperature affect the strength of the magnetic fields of the first inductor 504 and second inductor 512 equally, variations in the oil temperature do not result in a net difference between the strength of the magnetic field of the first inductor 504 and the strength of the magnetic field of the second inductor 512. Thus, variation due to temperature and other external environmental conditions are filtered from the comparison of differences detected between the first inductor 504 and the second inductor 512, while variations due to the presence of metal debris are detected.

The oil sensor 408 may determine a quantity of metal debris present in the oil reservoir based on the difference in peak voltage of the first inductor 504 and the second inductor 512. For example, higher overall amounts of metal debris (e.g., higher ratios of the volume of metal debris to the volume of oil) may result in a stronger net magnetic field generated by the entire amount (e.g., entire volume) of metal debris. Each individual piece of metal debris may experience eddy currents which contribute to the net magnetic field (e.g., combined magnetic field) generated by the entire volume of metal debris. Thus, a higher (e.g., stronger) net magnetic field generated by the entire volume of metal debris may be indicative of a higher number of individual pieces of metal debris within the entire volume, while a lower net magnetic field generated by the entire volume of metal debris may be indicative of a lower number of individual pieces of metal debris within the entire volume. Further detail regarding magnetic field generation, eddy current generation, and identification of metal debris presence/quantity is now described with reference to FIGS. 6-8.

Figure 6:
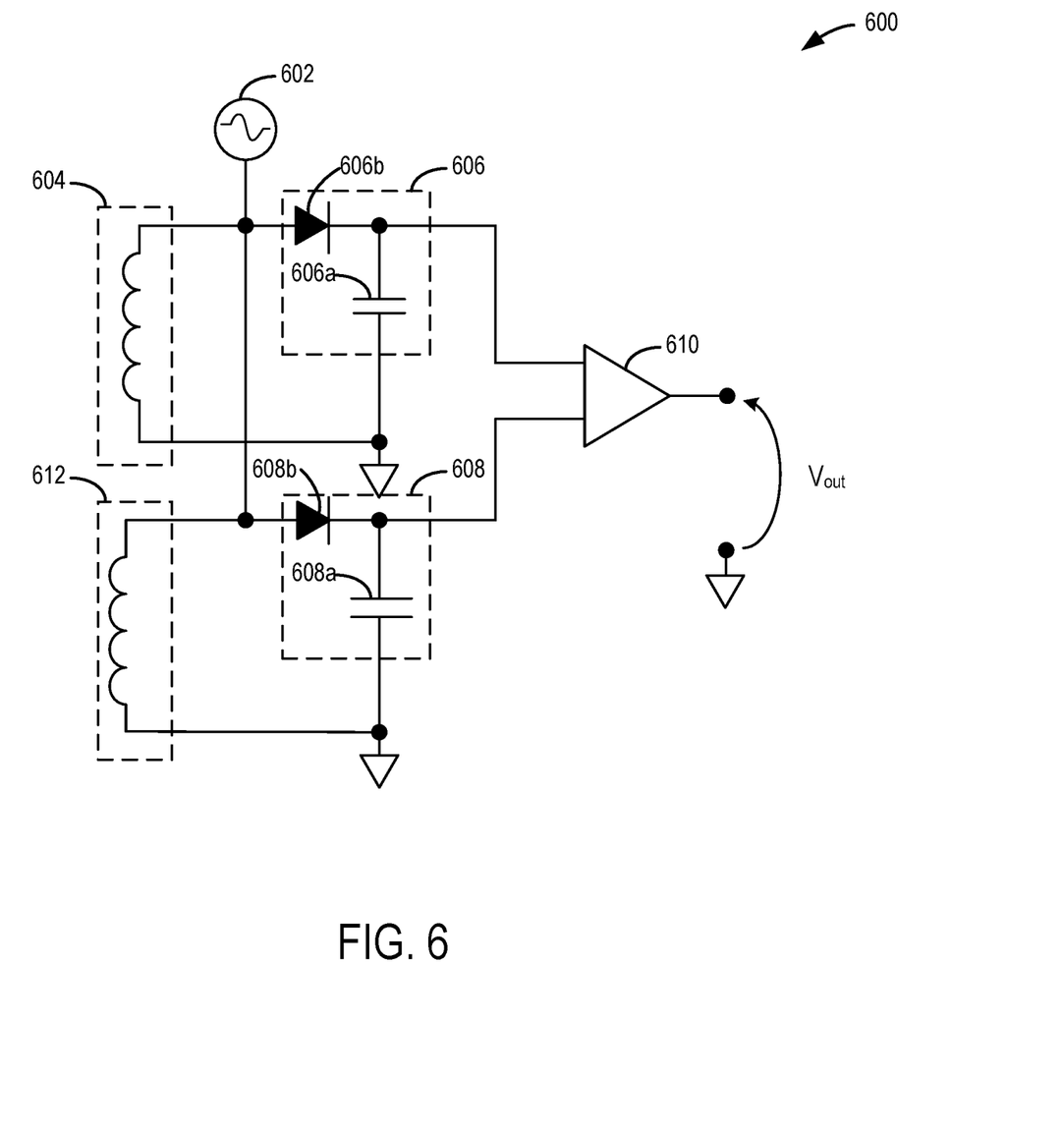
FIG. 6 shows a schematic representation of a circuit of the oil sensor of FIGS. 4-5.
Figure 7:
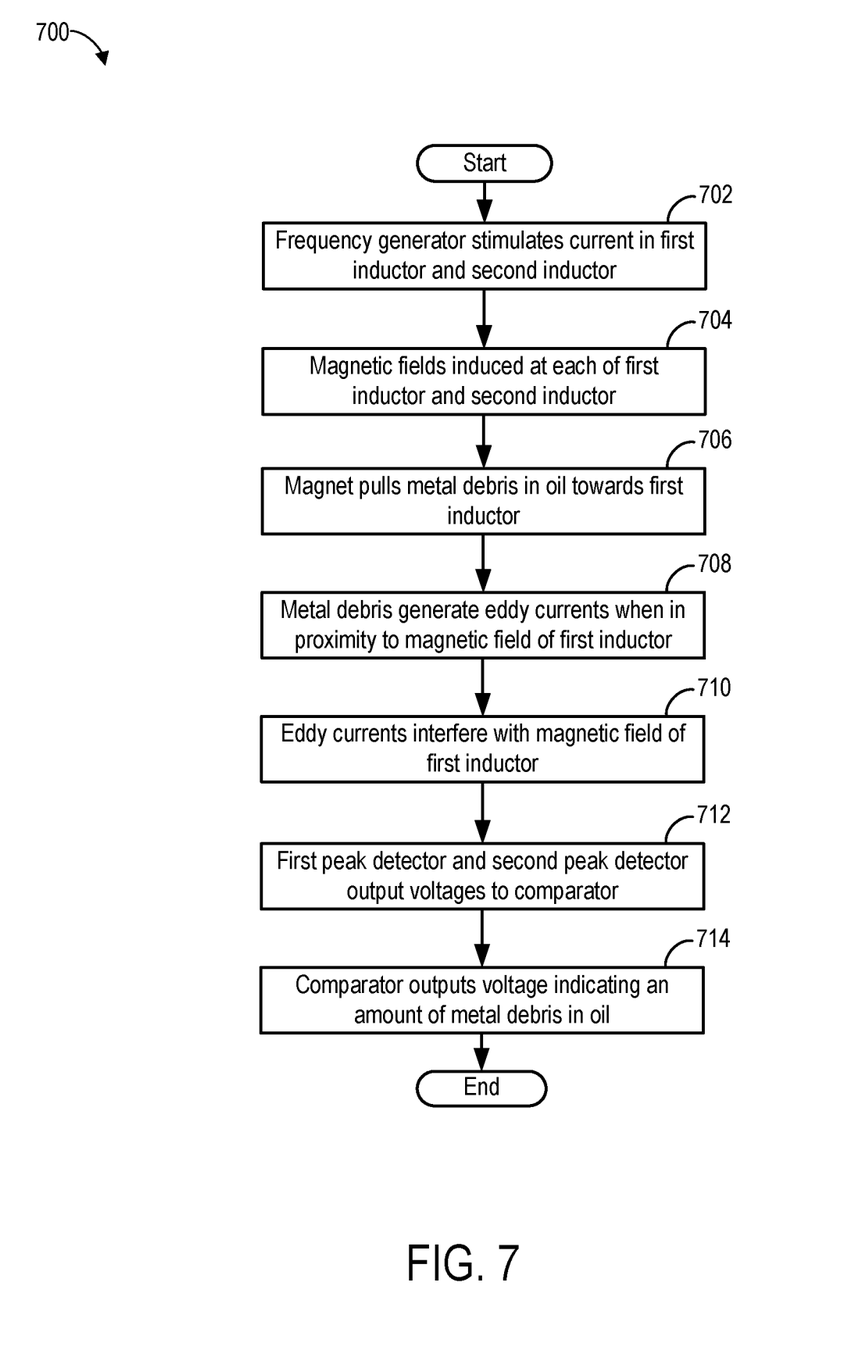
FIG. 7 illustrates a method for detecting deterioration of oil using the oil sensor depicted in FIGS. 4-6.

FIG. 6 shows a schematic representation of a circuit 600 of the oil sensor of FIGS. 4-5. The circuit 600 is an example of a circuit of the circuit board 514 positioned in the oil sensor 408 and electronically coupled to elements thereof as previously described and further elaborated on herein. For example, the circuit 600 is coupled to an external sensing element 604 and an internal comparison element 612. The external sensing element 604 is the first inductor 504 and the internal comparison element 612 is the second inductor 512 of FIG. 5. The circuit 600 includes a frequency generator 602, a first peak detector 606, a second peak detector 608, and a comparator 610. The circuit 600 may further include a series resistor to assist in controlling a maximum current which can be driven by the external sensing element 604 and the internal comparison element 612. The comparator 610 is connected to a control system, such as the control system 140 of FIG. 1 via connectors 511 of FIG. 5, and is further connected to ground.

The frequency generator 602 provides alternating electrical current (AC) to each of the external sensing element 604 and the internal comparison element 612, resulting in a magnetic field generated at each of the elements. The frequency generator 602 may provide a sinusoid wave electrical signal or a square wave electrical signal in some examples. When the external sensing element 604 and the internal comparison element 612 have the same structure, as described in FIG. 5, power used by the frequency generator 602 to generate the magnetic fields may be the same for both elements. Power used to generate a magnetic field may be influenced by boundary conditions, which may include temperature (e.g., of the oil), metallic objects in proximity to the magnetic field, influences of other inductors or currents flowing nearby, and so on. Thus, when no metallic objects are in proximity to a magnetic field of the external sensing element, power used to generate magnetic fields for the internal comparison element 612 and the external sensing element 604 may be equal. For example, as the internal comparison element 612 and the external sensing element 604 have the same structures they are thus affected in the same way by influences such as temperature, thereby compensating for the effect of temperature.

The external sensing element 604 is coupled to the first peak detector 606 and the internal comparison element 612 is coupled to the second peak detector 608. Both the external sensing element 604 and the internal comparison element 612 are connected to ground. Each of the peak detectors includes a capacitor and a diode, which are used to detect a peak voltage value across the respective element. The first peak detector 606 includes a first capacitor 606a and a first diode 606b. The second peak detector 608 includes a second capacitor 608a and a second diode 608b. Other peak detector configurations may be implemented which detect voltage peaks of the external sensing element 604 and the internal comparison element 612. The first peak detector 606 outputs a voltage indicating a peak voltage across the external sensing element 604, and the second peak detector 608 outputs a voltage indicating a peak voltage across the internal comparison element 612. An additional capacitor may be added to each peak detector to assist in reducing a power demand used to drive the respective external sensing element 604 or internal comparison element 612. The peak detectors thus detect and maintain the maximum voltage value seen across the respective element.

For example, the first peak detector 606 may detect a peak voltage of the AC signal provided to the first peak detector 606 by the external sensing element 604. The voltage may peak (e.g., be greater than a baseline voltage, as established by the internal comparison element 612) due to interference (e.g., attenuation) of the AC signal by a magnetic field generated by metal debris within the oil, as further described below. The first peak detector 606 outputs a voltage to the comparator 610 corresponding to the peak voltage of the external sensing element 604.

The voltage of the AC signal provided by the internal comparison element 612 may not substantially increase when metal debris are present in the oil, as the internal comparison element 612 is shielded by the external sensing element 604 and the external case 502 from effects of the magnetic field generated by the metal debris. The peak voltage detected by the external sensing element 604 may be equal to the voltage detected by the internal comparison element 612 when no or negligible metal debris is present in the oil. A difference between the peak voltage detected by the external sensing element 604 and the peak detected by the internal comparison element 612 may increase as the amount of metal debris within the oil increases. In other words, during conditions in which the oil includes no metal debris (e.g., no metal debris is within the oil reservoir 402 of FIG. 4), a peak amplitude (voltage) of the AC signal output by the internal comparison element 612 may be equal to a peak amplitude of the AC signal output by the external sensing element 604. During such conditions, the signal output to the comparator 610 by the first peak detector 606 indicating the voltage across the first peak detector 606 may be equal to the signal output to the comparator 610 by the second peak detector 608 indicating the voltage across the second peak detector 608. Outputs of the peak detectors are referred to a virtual ground generated at equation 1 by a designated quad-op-amp. In equation 1, V_CGND is a voltage collector (e.g., the external sensing element 604 or the internal comparison element 612) coupled to the virtual ground. V_CC is the voltage common collector.

$$V\_CGND = V\_CC/2 \quad (1)$$

Upon receiving the output signals of each of the first peak detector 606 and the second peak detector 608 (which may be referred to herein as inputs of the comparator 610), the comparator 610 may compare the output signals of each of the first peak detector 606 and the second peak detector 608 and amplify any difference between the outputs. For example, if the first peak detector 606 outputs a first voltage, the second peak detector 608 outputs a second voltage, and a difference between the first voltage and the second voltage is greater than a threshold difference, the comparator 610 may output a third voltage indicating above threshold difference between the external sensing element 604 and the internal comparison element 612. When the difference is greater than the threshold difference, it may be determined that a presence of metal debris in the oil is not negligible (e.g., may degrade elements of the system). The third voltage may indicate that the voltage of the external sensing element 604 had changed, which may be due to eddy currents induced by metal debris in the oil. In one example, the threshold difference is 1 mV and may be configurable based on an application of the oil sensor. The threshold difference may be a voltage other than 1 mV and may be configurable based on application of the oil sensor (e.g., depending on the system in which it is integrated) and/or operating conditions.

Additionally or alternatively, the comparator 610 may output a voltage value equal to the difference of the peaks sensed from the external sensing element 604 and the internal comparison element 612 and conditioned by the first peak detector 606 and the second peak detector 608, respectively (e.g., the first voltage and the second voltage). Thus, indication of metal debris presence and quantity is given by the voltage value provided by the comparator 610. The oil sensor may not implement a threshold difference and instead outputs the voltage value equal to the difference.

Further, the first voltage and the second voltage may be used to detect a presence and a quantity of metal debris in oil by comparing the third value with a lookup value table. The circuit of the oil sensor may be calibrated by acting on the lookup value table, which may be implemented by a manufacturer and thus allow the oil sensor to operate in different systems (e.g., any system having an oil lubrication device) and under different operating scenarios.

For example, when a conductive element (e.g., metal debris) is in the vicinity of the magnetic field of the external sensing element 604, the magnetic field induces circulating currents (e.g., eddy currents) on the conductive element, herein referred to as a target. Eddy currents of the target generate a magnetic field around the target, where a target magnetic field strength is based on a distance of the target from the external sensing element 604, and a size and shape of the target. The target magnetic field opposes the magnetic field of the external sensing element 604.

The oil sensor may thus measure a change in maximum voltage value across the external sensing element 604 based on the voltage output by the first peak detector 606. As the magnetic field of the internal comparison element 612 is shielded from eddy current effects, the voltage output by the second peak detector 608 may be unchanged when metal debris is present in the oil. When the voltages output by the first peak detector 606 and the second peak detector 608 are compared at the comparator 610, the resulting third voltage may be different than when voltage values are compared when metal debris is absent from the oil. The third voltage output by the comparator 610 may be used to determine a presence and quantity of metal debris in oil and further may be used to alert a user to a presence of metal debris, as further described in FIG. 8.

As briefly described above, other sources of voltage variations may induce parasitic phenomena due to electronic components of the sensor and temperature variation (e.g., varying temperature of the oil and/or of metal components of the oil sensor). Contribution of parasitic phenomena due to electronic components may be reduced by setting the input frequency value (e.g., from the frequency generator 602) to a desired value. The desired value may be determined based on a compromise between temperature stability (e.g., the frequency generator 602 is part of the sensor and thus experiences temperature variations along with other components of the sensor), desired effect of metal debris eddy current on the magnetic field of the external sensing element 604 relative to the internal comparison element 612, and ease of implementation of the frequency generator. The desired value may be different when the oil sensor is implemented in different systems, such as hybrid electric vehicles, electric vehicles, off highway axels, on highway axels, and so on. The oil sensor described herein is targeted to off highway axels.

Voltage variation due to temperature variation may be reduced by positioning of the external sensing element 604 and the internal comparison element 612, as described above. For example, temperature drift may impose variation of the linear output voltage (e.g., output from the external sensing element 604 and internal comparison element 612). Variation of the linear output voltage may be directly proportional to temperature drift. Both the internal comparison element 612 and the external sensing element 604 may be influenced in the same way by temperature and other external sources of noise which may result in output variation, due to their placement in close proximity to each other.

However, since the internal comparison element 612 is placed behind the external sensing element 604, and other elements of the oil sensor 408 as described above, the internal comparison element 612 is masked from effects of a presence of metal debris by the external sensing element 604, as described above.

The circuit 600 may manage outputs of both the external sensing element 604 and the internal comparison element 612 to address small differences in inductance due to constructive processes of the inductors or potential temporary imbalance caused by rapid temperature changes. For example, the external sensing element 604 may be configured to present a higher inductance value or a lower inductance value with respect to the internal comparison element 612. Inductance may thus be modeled as a fixed part plus a variable part dependent on a presence of a target, a distance between the target and the external sensing element 604, and dimensions of the target. The model may further include a fixed resistance characteristic of the external sensing element 604 plus a contribution due to the target, and dependent on distance, in series to an ideal inductance (e.g., the internal comparison element 612).

FIG. 7 illustrates a method 700 for detecting deterioration of oil (e.g., a presence of metal debris) using the oil sensor depicted in FIGS. 4-6. The method 700 may be a high level description of the process conducted by the oil sensor 408 to detect metal debris in the oil, thus components of the oil sensor described in the method 700 may refer to components of the oil sensor 408.

At 702, the method 700 includes the frequency generator 602 stimulating current in the first inductor 504 and the second inductor 512. As described above, the first inductor is referred to as the external sensing element 604 and the second inductor is referred to as the internal comparison element 612 in the circuit 600. Both the first inductor and the second inductor are stimulated with the same current induced by the voltage modulated signal generated by the frequency generator.

At 704, the method 700 includes magnetic fields being induced at each of the first inductor and the second inductor. Current at the first inductor may induce a first magnetic field and current at the second inductor may induce a second magnetic field. A first voltage of the first inductor may be measured by the first peak detector 606 and a second voltage of the second inductor may be measured by the second peak detector 608. Prior to metal debris being in proximity to the oil sensor, for example, prior to metal debris entering the oil reservoir 402, the first voltage and the second voltage may be equal. When the first voltage and the second voltage are equal, a third voltage output by the comparator 610 may indicate to a controller of a system in which the oil sensor is positioned that metal debris is not detected by the oil sensor. For example, the oil sensor may be coupled to the controller 141 of the vehicle 100 of FIG. 1, as described in FIGS. 4-6.

If metal debris is present in oil and metal debris enters the oil reservoir, at 706, the method 700 includes the magnet 508 pulling the metal debris towards the first inductor. The first inductor is exposed to oil and thus effects of the metal debris on the first voltage of the first inductor, as further described below, may be detected by the first inductor.

At 708, the method 700 includes the metal debris in proximity to the first inductor generating eddy currents when in proximity to the first magnetic field. For example, each piece of metal debris in proximity to the first magnetic field may generate its own eddy current, and each eddy current may be in contrast to the first magnetic field.

At 710, the method 700 includes the eddy currents of the metal debris interfering with the first magnetic field of the first inductor. For example, as the eddy currents are in contrast with the first magnetic field, generation of the eddy currents may result in a change in the first voltage of the first inductor. As the second inductor is shielded from the effects of the metal debris by the first inductor and by the external case, the second voltage may be unchanged.

At 712, the method 700 may include the first peak detector outputting the first voltage and the second peak detector outputting the second voltage to the comparator. As described above, the first voltage may be a different value compared to when metal debris was not present in the oil, and the second voltage may be unchanged. Thus, the first voltage and the second voltage may be different, unequal values.

At 714, the method 700 includes the comparator outputting a third voltage indicating an amount of metal debris in oil. When the first voltage and the second voltage are approximately equal, the third voltage may be a first value equal to V_CC/2, as described in equation 1. When the first voltage and the second voltage are substantially different, the third voltage may be a second value. As further described in FIG. 8, the first value may indicate an absence of metal debris in the oil and the second value may indicate a presence of metal debris in the oil.

Figure 8:
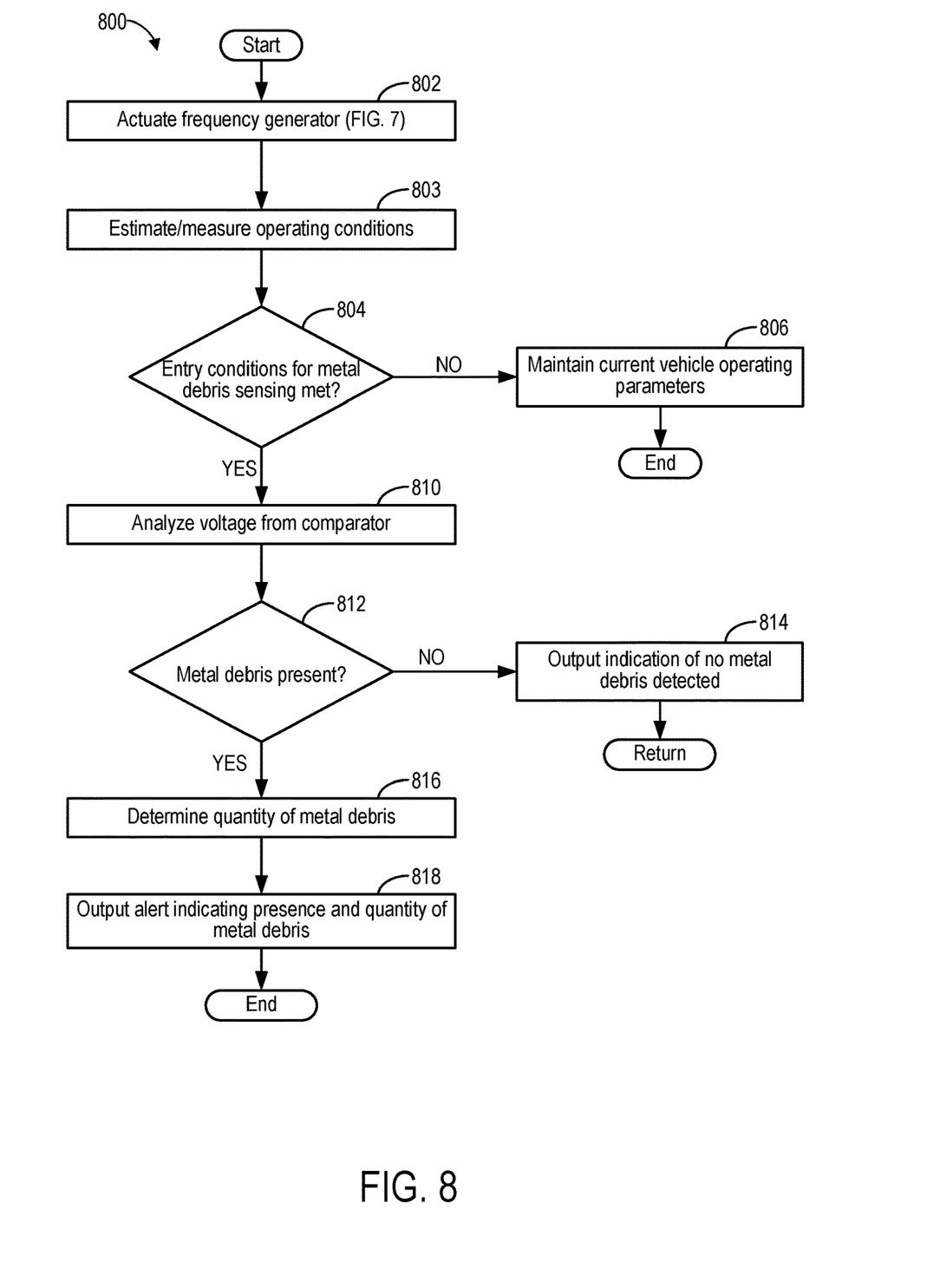
FIG. 8 illustrates a method for determining a presence and quantity of metal debris in oil using the oil sensor depicted in FIGS. 4-6.

A method 800 of FIG. 8 may be implemented by a controller, such as the controller 141 of FIG. 1 which includes a processor 142 and a memory 144. The memory may hold instructions stored therein that, when executed by the processor, cause the controller to determine a presence and quantity of metal debris in oil using the oil sensor depicted in FIGS. 4-6. As described in the method 700 of FIG. 7, the comparator of the oil sensor may compare voltages detected by the first inductor and the second inductor and output a value equal to the difference between the first voltage of the first inductor and the second voltage of the second inductor. The third voltage of the comparator may be output to the processor, which may perform the method 800 of FIG. 8 to determine the presence and quantity of metal debris in the oil. The method 800 may further include alerting a user to the presence and quantity of metal debris.

The oil sensor may be in an 'on' state when the frequency generator is actuated to provide current to each of the first inductor and the second inductor to induce magnetic fields used to detect an amount of metal debris in the oil. At 802, the method 800 includes actuating the frequency generator, as described in method 700 of FIG. 7. Actuating the frequency generator may include providing a voltage to the frequency generator, which may then generate a sinusoid or square wave. As described in the method 700, the comparator outputs a voltage based on the difference between the first voltage and the second voltage of the first inductor and the second inductor, respectively.

At 803, the method 800 includes estimating system operating conditions. When the oil sensor is implemented in a lubricating system of a vehicle, such as the vehicle 100 of FIG. 1, estimating operating conditions may include estimating oil temperature, whether the oil is circulating in the lubricating system or is stagnant, and so on.

At 804, the method 800 includes determining if entry conditions have been met for metal debris sensing. For example, entry conditions may include operating conditions estimated/measured at 803, such as the oil temperature being above a threshold temperature, where the threshold temperature may be 250° F. Entry conditions may further include that the oil is circulating through the lubrication system, a duration has elapsed since a last oil change, and so on. If entry conditions are not met, the method 800 proceeds to 806, where the method 800 includes maintaining current vehicle operating parameter's. The oil sensor is thus not used to determine a presence of metal debris in the oil. The method 800 ends.

If at 804, entry conditions have been met, the oil sensor is used to determine a presence of metal debris in the oil. At 810, the method 800 includes analyzing the voltage from the comparator (e.g., the difference between the first voltage of the first inductor and the second voltage of the second inductor). The voltage is used to determine a presence and quantity of metal debris in the oil.

At 812, the method 800 includes determining if metal debris is present. In one example, metal debris may be present in oil when the third voltage is above a positive, non-zero threshold value, such as VCC/2+2 mV. If the third voltage is below the threshold value, metal debris may not be detected by the oil sensor and therefore may not be present in the oil. If the third voltage is greater than or equal to the threshold value, metal debris may be detected by the oil sensor.

If metal debris is not present, the method 800 proceeds to 814, where the method 800 includes outputting indication that no metal debris has been detected. For example, an indication may appear to a vehicle operator at a heads up display or other user interface that the oil is not degraded. In another example, the absence of a malfunction indicator light (MIL) may be interpreted by a user as a lack of oil degradation. When the oil sensor is implemented in a system other than a vehicle, the indication may be output to an external device. Whether or not a user is alerted to a lack of metal debris in the oil, the output indicating a status of oil degradation (or lack thereof) may be stored in the memory of the controller, along with a date and time at which the method was implemented.

Returning to 812, if it is determined that metal debris is present in the oil, the method 800 proceeds to 816. At 816, the method 800 includes determining a quantity of metal debris present in the oil. In one example, the quantity may be determined based on the third voltage where a value of the third voltage may be mapped to a relative quantity of metal debris in the oil.

At 818, the method 800 includes outputting an alert indicating the presence of metal debris. The alert may further include indication of the quantity of metal debris. A MIL may be illuminated, indicating degradation of oil. Further, a relative quantity of metal debris and/or an amount by which oil is degraded may be displayed to the user in a heads up display or other user interface. The alert may include indication that an oil replacement is desired to reduce further degradation of the oil and/or the vehicle system.

In this way, an oil sensor may be used to detect metal debris suspended in oil of a lubrication system based on inductance differences across two inductors of a circuit. Variations due to temperature variations may be reduced due to positioning of the two inductors in the oil sensor. The herein described oil sensor may have a reduced footprint and complexity compared to conventional oil sensors. As elements of the oil sensor are contained in housing, the oil sensor may be placed in a variety of environments, for example, in a channel of a lubrication system, in an oil reservoir, and so on. Mechanical deterioration may be reduced, as implementation of the herein described oil sensor may alert a user to a presence of metal debris in the oil and thus indicate a request for oil to be cleaned and/or replaced, which may remove the metal debris from the oil and reduce further degradation due to the cycling of metal debris through the lubrication system.

The disclosure also provides support for a system for metallic debris detection, comprising: a detection circuit including a first inductor and a second inductor, the second inductor shielded from an external environment, wherein the detection circuit generates an output based on a difference between a first voltage of the first inductor and a second voltage of the second inductor, where the difference indicates a presence of metallic debris within oil. In a first example of the system, the detection circuit comprises a first peak detector coupled to the first inductor, a second peak detector coupled to the second inductor, each of the first peak detector and the second peak detector coupled to a comparator, and each of the first inductor, the first peak detector, the second inductor, and the second peak detector are coupled to ground. In a second example of the system, optionally including the first example, the comparator compares voltages of the first inductor and the second inductor, as output by the first peak detector and the second peak detector respectively, to identify the difference between the first voltage and the second voltage. In a third example of the system, optionally including one or both of the first and second examples, the detection circuit is coupled to a control system which takes the difference between the first voltage and the second voltage as an input and uses the input to determine information about the presence and a quantity of metallic debris. In a fourth example of the system, optionally including one or more or each of the first through third examples, the first inductor is exposed to oil. In a fifth example of the system, optionally including one or more or each of the first through fourth examples, the second inductor is positioned behind the first inductor such that the second voltage of the second inductor is shielded from the external environment by the first inductor and an external case. In a sixth example of the system, optionally including one or more or each of the first through fifth examples, the system further comprises: a first spacer, a magnet, a second spacer, and a circuit board comprising the detection circuit, where the first spacer is between the first inductor and the magnet, and the second spacer is positioned between the magnet and the second inductor. In a seventh example of the system, optionally including one or more or each of the first through sixth examples, the first spacer, the magnet, the second spacer, the circuit board, the first inductor, and the second inductor are housed in an external case. In an eighth example of the system, optionally including one or more or each of the first through seventh examples, the external case formed of metal or non-magnetically inert material to shield the second inductor from the external environment. In a ninth example of the system, optionally including one or more or each of the first through eighth examples, the first inductor and the second inductor are each coupled to the circuit board via an electrical lead connection.

The disclosure also provides support for a method, comprising: pulling metal debris towards an external sensing element using a magnet, inducing a first magnetic field at the external sensing element and a second magnetic field at an internal comparison element, and comparing voltages of the external sensing element and the internal comparison element at a comparator to detect metal debris suspended in oil. In a first example of the method, metal debris in proximity to the external sensing element and subjected to the first magnetic field generate eddy currents opposing the first magnetic field. In a second example of the method, optionally including the first example, the eddy currents opposing the first magnetic field change a voltage of the external sensing element. In a third example of the method, optionally including one or both of the first and second examples, the second magnetic field is shielded by the external sensing element and a metallic case from eddy current effects. In a fourth example of the method, optionally including one or more or each of the first through third examples, the method further comprises: outputting an indication of a presence and a quantity of metal debris in oil to an external device when the voltages of the external sensing element and the internal comparison element are different. In a fifth example of the method, optionally including one or more or each of the first through fourth examples, the method further comprises: determining the presence and the quantity of metal debris in oil by comparing an output value with a lookup value table or threshold, and outputting the quantity at the external device. In a sixth example of the method, optionally including one or more or each of the first through fifth examples, the quantity of metal debris is a relative quantity. In a seventh example of the method, optionally including one or more or each of the first through sixth examples, outputting the quantity includes outputting a level of oil degradation. In an eighth example of the method, optionally including one or more or each of the first through seventh examples, the method further comprises: outputting an indication of an absence of metal debris in oil when the voltages of the external sensing element and the internal comparison element are equal.

The disclosure also provides support for a system, comprising: a lubricating system including an oil sensor, and a controller with instructions stored in non-transitory memory, that when executed, cause the controller to: induce a first magnetic field at an external sensing element and a second magnetic field at an internal comparison element, and detect a presence and a quantity of metal debris suspended in oil by comparing a first voltage of the external sensing element and a second voltage of the internal comparison element at a comparator.

FIGS. 1-6 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

It will be appreciated that the configurations and routines disclosed herein are exemplary in nature, and that these specific embodiments are not to be considered in a limiting sense, because numerous variations are possible. Moreover, unless explicitly stated to the contrary, the terms "first," "second," "third," and the like are not intended to denote any order, position, quantity, or importance, but rather are used merely as labels to distinguish one element from another. The subject matter of the present disclosure includes all novel and non-obvious combinations and sub-combinations of the various systems and configurations, and other features, functions, and/or properties disclosed herein.

As used herein, the term "approximately" is construed to mean plus or minus five percent of the range unless otherwise specified.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A system for metallic debris detection, comprising:
a detection circuit including a first inductor and a second inductor; and
an external case with the detection circuit housed therein, wherein the external case and the first inductor form a barrier between the second inductor and air and/or oil such that the second inductor is shielded from metal debris influences by the external case and by the first inductor, wherein the detection circuit generates an output based on a difference between a first voltage of the first inductor and a second voltage of the second inductor, where the difference indicates a presence of metallic debris within oil, and wherein the air and/or oil are external to the external case.

2. The system of claim 1, wherein the detection circuit comprises a first peak detector coupled to the first inductor and configured to detect voltage peaks in the first voltage of the first inductor, a second peak detector coupled to the second inductor and configured to detect voltage peaks in the second voltage of the second inductor, each of the first peak detector and the second peak detector coupled to a comparator that is configured to compare the first voltage and the second voltage, and each of the first inductor, the first peak detector, the second inductor, and the second peak detector are coupled to ground.

3. The system of claim 2, wherein the comparator compares the first voltage of the first inductor and the second voltage of the second inductor, as output by the first peak detector and the second peak detector respectively, to identify the difference between the first voltage and the second voltage.

4. The system of claim 3, wherein the detection circuit is coupled to a control system, where the control system is configured to calculate the difference between the first voltage and the second voltage, and uses the difference to determine information about the presence and a quantity of metallic debris.

5. The system of claim 1, wherein the first inductor is exposed to oil.

6. The system of claim 1, wherein the second inductor is positioned behind the first inductor such that the second voltage of the second inductor is shielded from metal debris influences by the first inductor and the external case.

7. The system of claim 1, further comprising a first spacer, a magnet, a second spacer, and a circuit board comprising the detection circuit, where the first spacer is between the first inductor and the magnet, and the second spacer is positioned between the magnet and the second inductor.

8. The system of claim 7, wherein the first spacer, the magnet, the second spacer, the circuit board, the first inductor, and the second inductor are housed in the external case.

9. The system of claim 1, wherein the external case is formed of metal or other non-magnetically inert material to shield the second inductor from metal debris influences.

10. The system of claim 7, wherein the first inductor and the second inductor are each coupled to the circuit board via an electrical lead connection.

11. A method, comprising:
pulling metal debris towards a first inductor using a magnet having a magnetic field;
selectively inducing a first magnetic field via the first inductor and a second magnetic field via a second inductor; and
comparing a first voltage of the first inductor and a second voltage of the second inductor at a comparator, where the first voltage of the first inductor changes in response to metal debris being present in the first magnetic field, to detect metal debris suspended in oil.

12. The method of claim 11, wherein the metal debris in proximity to the first inductor and subjected to the first magnetic field generate eddy currents opposing the first magnetic field.

13. The method of claim 12, wherein the eddy currents opposing the first magnetic field change a voltage of the first inductor.

14. The method of claim 12, wherein the second magnetic field is shielded by the first inductor and by a metallic case from eddy current effects.

15. The method of claim 11, further comprising outputting an indication of a presence and a quantity of metal debris in oil to a device when the first voltage of the first inductor and the second voltage of the second inductor are different.

16. The method of claim 15, further comprising determining the presence and the quantity of metal debris in oil by comparing an output value with a lookup value table or threshold, and outputting the quantity at the external device.

17. The method of claim 16, wherein the quantity of metal debris is a relative quantity.

18. The method of claim 16, wherein the outputting of the quantity includes outputting a level of oil degradation.

19. The method of claim 11, further comprising outputting an indication of an absence of metal debris in oil when the first voltage of the first inductor and the second voltage of the second inductor are equal.

20. A system, comprising:
a lubricating system including an oil sensor comprising a first inductor that is exposed to oil, and a second inductor that is shielded from being exposed to oil at least in part by the first inductor; and
a controller with instructions stored in non-transitory memory, that when executed, cause the controller to:
induce a first magnetic field at the first inductor and a second magnetic field at the second inductor; and
detect a presence and a quantity of metal debris suspended in oil by comparing a first voltage of the first inductor and a second voltage of the second inductor at a comparator.

* * * * *